United States Patent
Wohleb (10) Patent No.: US 9,200,991 B2
(45) Date of Patent: Dec. 1, 2015

(54) SORPTIVE EXTRACTION LAYER FOR IMMOBILIZED LIQUID EXTRACTION

(71) Applicant: Tecan Trading AG, Mannedorf (CH)

(72) Inventor: Robert Wohleb, El Dorado Hills, CA (US)

(73) Assignee: TECAN TRADING AG, Mannedorf (CH)

( * ) Notice: Subject to any disclaimer, the term of this patent is extended or adjusted under 35 U.S.C. 154(b) by 203 days.

(21) Appl. No.: 13/909,447

(22) Filed: Jun. 4, 2013

(65) Prior Publication Data
US 2014/0356976 A1 Dec. 4, 2014

(51) Int. Cl.
| | |
|---|---|
| *B01L 3/00* | (2006.01) |
| *G01N 1/34* | (2006.01) |
| *C09D 135/02* | (2006.01) |
| *G01N 1/40* | (2006.01) |
| *G01N 30/00* | (2006.01) |

(52) U.S. Cl.
CPC ........... *G01N 1/34* (2013.01); *C09D 135/02* (2013.01); *G01N 1/405* (2013.01); *B01L 3/50255* (2013.01); *Y10T 436/255* (2015.01)

(58) Field of Classification Search
CPC ........ G01N 1/405; B01D 15/08; B01D 15/20; B01D 15/206; B01D 15/265; B01D 15/42; B01D 15/424; B01D 15/426
See application file for complete search history.

(56) References Cited

U.S. PATENT DOCUMENTS

| | | | |
|---|---|---|---|
| 6,225,073 B1 * | 5/2001 | Alexander et al. | 435/7.93 |
| 8,057,668 B2 * | 11/2011 | Gjerde et al. | 210/198.2 |
| 2004/0185445 A1 | 9/2004 | Fang | |
| 2005/0047976 A1 * | 3/2005 | Gubernator et al. | 422/130 |
| 2005/0059162 A1 | 3/2005 | Wohleb | |
| 2006/0110295 A1 * | 5/2006 | Wohleb | 422/101 |
| 2010/0256005 A1 * | 10/2010 | Petrik et al. | 506/9 |
| 2011/0042317 A1 | 2/2011 | Gjerde et al. | |

FOREIGN PATENT DOCUMENTS

| | | |
|---|---|---|
| EP | 0 882 984 A1 | 12/1998 |
| EP | 2649455 A1 * | 10/2013 |

OTHER PUBLICATIONS

Electron Microscopy Sciences (Herein EMS, see PDF attached), Feb. 7, 2009.*
Wells (Apr. 2000, Handling Large Volume Samples: Applications of SPE to Environmental Matricies), pp. 1-27.*
Truei et al. (1992, Advances in Biochemical Engineering/Biotechnology, vol. 47, pp. 1-44).*
International Search Report of International Application No. PCT/EP2014/060295.
Sorptive Sample Preparation, E. Baltussen, et al., Apr. 9, 2002.

(Continued)

*Primary Examiner* — Allison Fitzsimmons
(74) *Attorney, Agent, or Firm* — Notaro, Michalos & Zaccaria P.C.

(57) ABSTRACT

A sorptive extraction layer for immobilized liquid extraction of target molecules preferably from biological samples is disclosed. The sorptive extraction layer is mainly composed of ethylene-acrylate-copolymer. Preferably, microplate wells are at least partially coated with such a sorptive extraction layer. There is also disclosed a method of extracting target molecules preferably from biological samples. According to this method, immobilized liquid extraction is carried out with a sorptive extraction layer which is mainly composed of ethylene-acrylate-copolymer.

20 Claims, 4 Drawing Sheets

(56) References Cited

OTHER PUBLICATIONS

Simplified Extraction of Drugs from Serum Using Immobilized Liquid Extraction 96-Well Plates, ILE, Immobilized Liquid Extraction, Jun. 2007.

Extraction of Methadone & Imipramine from Serum Using Immobilized Liquid Extraction (ILE) Well Plates.

Octanol-Water Partition Coefficients of Simple Organic Compounds, James Sangster, Jan. 30, 1989.

Standard for Microplates—Footprint Dimensions, ANSI, American National Standards Institute.

* cited by examiner

SORPTIVE EXTRACTION LAYER FOR IMMOBILIZED LIQUID EXTRACTION

FIELD OF TECHNOLOGY

The present invention relates to a sorptive extraction layer for immobilized liquid extraction of target molecules preferably from biological samples, and preferably to a micro-plate with such a sorptive extraction layer in its wells, as well as to a method of extracting target molecules preferably from biological samples utilizing immobilized liquid extraction with a sorptive extraction layer.

BACKGROUND OF THE INVENTION

In biological samples, target molecules (also called analytes) of interest to be identified and quantified are for example vitamins, hormones, drugs, medication, odorous substances, flavoring substances, pesticides, pollutants or any organic compounds. The molecular weight of such target molecules is in most cases below 1000 Da (Da=Dalton=g/mol). Such target molecules may be contained in biomedicine samples, in body fluids (e.g. blood, blood serum, urine), in food (especially beverages), in drinking water or waste water. All those samples, which preferably are liquid and in general have an aqueous matrix, are referred to as biological samples, which are preferred in the present patent application.

The target molecules often are present only as trace substances in the samples. Therefore a method of accumulation has to be applied first, before the concentrated target molecules can be analyzed by a determination method such as gas chromatography (GC), or liquid chromatography (LC, HPLC), or gas chromatography linked with mass spectrometry (GC-MS), or liquid chromatography linked with mass spectrometry (LC-MS). As a method of accumulation, the extraction of target molecules from biological samples by a sorbent, in particular by a sorptive extraction layer, can be applied. Such sorptive extraction layer materials preferably have no pores, but are polymeric materials with low enough glass transition point (Tg), so that the application temperature is above their glass transition point. Above Tg the polymers are in a gum-like or liquid-like flexible state. In this state analytes can enter such homogeneous, non-porous polymers and dissolve in the bulk of the polymer phase.

RELATED PRIOR ART

A good overview over the fundamentals is given in the article "Sorptive sample preparation—a review" by E. Baltussen, C. A. Cramers, P. J. F. Sandra; Anal Bioanal Chem (2002) 373:3-22; published online 9 Apr. 2002 © Springer-Verlag 2002. Depending on the object which is coated by the sorptive extraction layer, the method is called open-tubular trapping (OTT) if the inside of a column or a capillary is sorbent-coated, or it is called solid-phase micro-extraction (SPME) if a fused-silica fiber is coated with a sorbent layer, or it is called stir-bar sorptive extraction (SBSE) if the glass jacket of a magnetic stirring rod is coated with a sorbent layer. Typical for SPME and SBSE is the static sampling which tends to reach an equilibrium in the partition of the analyte between the two phases, i.e. the sorbent or extractant phase and the liquid sample phase. The equilibrium constant is $K=C_E/C_S$, where $C_E$ is the concentration of analyte in the extractant and $C_S$ is the concentration of analyte in the sample in the equilibrium state. Rewriting leads to $K=(m_E/m_S)\times\beta$, where $m_E$ is the mass of analyte in the extractant, $m_S$ is the mass of analyte remaining in the sample, and $\beta$ is the volume phase ratio $V_S/V_E$. A further mathematical conversion leads to the expression for the extraction efficiency $\eta=m_E/m_{tot}=m_E/(m_E+m_S)$ which gives $\eta=1/[(\beta/K)+1]$. This means in order to achieve a high percentage of extracted analyte, K should be large and $\beta$ should be small. The higher K the better is the affinity of the analyte to the sorbent compared to the liquid sample phase. A smaller $\beta$ means less sample volume per sorbent volume, or expressed the other way round a higher ratio of sorbent to sample volume. Under the SBSE conditions with a relatively high amount of sorbent on a magnetic stir-bar, the $\beta$ value is about 100, whereas under the SPME conditions the $\beta$ value is about $2\times10^4$. This means that SBSE is an improvement with regard to sensitivity and quantitative extraction. Referring to K again, a suitable sorbent with high affinity has to be used. The recommended standard sorbent in the review article is polydimethylsiloxane (PDMS). PDMS is characterized as rather apolar (similar to octanol, K values comparable with known $K_{O/W}$). The polar polybutylacrylate is mentioned as alternative material for more polar analytes which have less affinity for PDMS. Another aspect is the time required for reaching the partition or distribution equilibrium; the diffusion of analytes from the sample into the extractant can be promoted by stirring or shaking. Although such mixing motion was applied for preparing the samples for the analysis, an equilibration time of 30 to 60 minutes was required.

Multiwell plates (microplates) coated with a sorbent material are known from the patent application published as U.S. 2006/0110295 A1. Each well of a microplate (which usually has a fixed format, e.g. with 96 wells) is coated on the interior wall or on the bottom surface or both. A sample is introduced into the wells, and an analyte is extracted from the sample matrix by exposing the sample to the sorbent coating of the well plate. After partitioning of the analyte into the sorptive material, the remaining sample is removed from the well, and later on an elution solvent is used for back-extracting the compound of interest respectively the analyte from the sorptive coating. In the preferred embodiment, the sorptive coating according to this document is a hydrophobic coating such as an immobilized polysiloxane, for example polydimethylsiloxane (PDMS).

The use of a polyacrylate phase for immobilized liquid extraction with coated 96-well microplates is disclosed in "The Application Notebook", June 2007, page 14, Biological, Advertising Supplement, title: "Simplified Extraction of Drugs from Serum Using Immobilized Liquid Extraction 96-Well Plates". It is mentioned that polyacrylate is a very polar phase for extracting highly water-soluble compounds. A drawback might be that the back-extraction efficiency and thus the overall recovery (which is the mathematical product of extraction efficiency and back-extraction efficiency) of the analyte are possibly reduced by the strong polar absorption forces.

Immobilized liquid extraction with well plates is described in more detail in the article "Extraction of Methadone & Imipramine from Serum Using Immobilized Liquid Extraction (ILE) Well Plates", which is available as PDF-document in the internet. Three types of polysiloxanes were alternatively used as immobilized extracting phases (coating) in the wells: Polydimethylsiloxane (PDMS), polydiphenylsiloxane and polytrifluoropropylmethylsiloxane. Even when intensely agitated by a vortexer at 3000 rpm, an extraction time of 45 minutes was required to approximately reach the extraction equilibrium, which is in the time range of the cited review article.

OBJECTS AND SUMMARY OF THE PRESENT INVENTION

In view of the related prior art discussed above which includes certain drawbacks or problems, it is an object of the present invention to suggest an alternative sorptive extraction layer for immobilized liquid extraction of target molecules preferably from biological samples, and preferably a microplate with such an alternative sorptive extraction layer in its wells, so that the alternative sorptive extraction layer optimizes the affinity and also the extraction efficiency and overall recovery for certain target molecules. It is also an object of the present invention to propose an improved or at least alternative method to carry out the extraction of target molecules preferably from biological samples utilizing immobilized liquid extraction.

This object is achieved in that an alternative sorptive extraction layer for immobilized liquid extraction of target molecules preferably from biological samples is proposed which is mainly composed of ethylene-acrylate-copolymer. "Mainly composed of" means that the alternative sorptive extraction layer according to the present invention consists to at least 90 weight-%, preferably to at least 95 weight-% of ethylene-acrylate-copolymer.

The term "ethylene-acrylate-copolymer" means that at least one type of ethylene-acrylate-copolymer is present, but it comprises also mixtures of more than one ethylene-acrylate-copolymer.

Preferably, the ethylene-acrylate-copolymer of the sorptive extraction layer is an amorphous ethylene-acrylate-elastomer, also known under the abbreviation AEM. It is particularly preferred if the amorphous ethylene-acrylate-elastomer is an amorphous ethylene-methylacrylate-dipolymer. In another particularly preferred embodiment the amorphous ethylene-acrylate-elastomer is an amorphous ethylene-methylacrylate-terpolymer.

In an alternative preferred variant the ethylene-acrylate-copolymer is a partially crystalline ethylene-acrylate-copolymer. In this variant it is particularly preferred if the partially crystalline ethylene-acrylate-copolymer is a partially crystalline ethylene-methylacrylate-copolymer.

In principle a sorptive extraction layer according to the invention can be applied as coating for any object which is suitable for carrying out a sorptive sample preparation, e.g. also as a coating for a magnetic stir-bar in SBSE, or in SPME, or in OTT. Other examples are coated particles, e.g. coated beads, for chromatography columns. The preferred object are microplates, and preferably, the wells of microplates are at least partially coated with a sorptive extraction layer according to the invention.

Microplates usually are standard microplates with normalized dimensions and standardized array of the wells according to the ANSI/SBS standard 1-2004. Microplates according to this standard are preferred, although other standards may also be accepted.

In particular, concerning a microplate with an array of wells, the wells comprise a bottom and a wall. At least a part of the bottom of at least a part of the wells is coated with a sorptive extraction layer according to the invention. It is preferred that the bottom and at least a part of the wall of the wells is coated with a sorptive extraction layer according to the invention. In this embodiment it is especially preferred if the sorptive layer has a mean thickness in the range of 10 to 100 µm.

An improved or at least alternative method of extracting target molecules preferably from biological samples utilizes immobilized liquid extraction comprising an extraction step with a sorptive extraction layer which is composed of ethylene-acrylate-copolymer.

Carrying out this method, preferably an extraction solvent mixture comprising water and an organic solvent is prepared. Preferably this extraction solvent mixture is mixed with a sample to form a combined solution. In most cases, water is the main component (i.e. greater than 50 vol-%) in said combined solution. The extraction solvent mixture not necessarily is a solution but could also be an emulsion. Preferably, the organic solvent used in the extraction solvent mixture is selected from the group consisting of acetonitrile, methanol, ethanol and isopropanol. Acetonitrile is the particularly preferred organic solvent.

Preferably the method is carried out in that the organic solvent concentration in the combined solution lies in a range between a minimum concentration of 10 vol-% and a maximum concentration of 35 vol-%, this range providing a release of the target molecules from possibly present proteins and enabling the target molecules to be attracted by and to partition into the sorptive extraction layer. At the same time, non-precipitating conditions can be maintained in this range.

In preferred variants the extraction solvent mixture additionally comprises at least one substance selected from the group consisting of buffers, salts, pH modifying agents and internal standards. Salt can serve for stabilizing possibly present proteins in solution, and can also have a positive influence on the analyte partition ratio, as it was observed with LiCl (Lithium chloride).

In a preferred embodiment of the method, the sorptive extraction layer is a coating on the inner surface of microplate wells, and agitation is applied for accelerating the extraction velocity during the extraction step. In a particularly preferred embodiment of the method, the coating covers the bottom and the wall to at least 40% of the inner height of the wells, the applied agitation is a vortexing at 1000 rpm or higher, and extraction under vortexing is carried out for a maximum of 20 minutes.

It is part of the method that the extraction step is usually followed by a washing step and a back-extraction step. For the back-extraction of the target molecules from the sorptive extraction layer, preferably a mixture of an organic solvent and water is used as elution solvent. The concentration of the organic solvent in the elution solvent is preferably higher than 50 vol-%.

In a preferred embodiment of the method, the sorptive extraction layer is a coating on the inner surface of microplate wells, and agitation is applied during the washing step and the back-extraction step.

Additional and inventive features, preferred embodiments, and variants of the sorptive extraction layer, of accordingly coated microplates, and of the method for extracting target molecules from preferably biological samples derive from the detailed description and specification of the invention as well as from the set of claims.

BRIEF DESCRIPTION OF THE FIGURES

The invention is explained with the help of the attached figures that show selected and exemplary embodiments of the present invention compared to prior art, without narrowing the scope and gist of this invention. It is shown in.

DETAILED DESCRIPTION OF THE PRESENT INVENTION

The characteristics and advantages of the present invention will become more apparent from the detailed description given hereinafter. However it should be understood that the detailed description and specific examples, while indicating preferred embodiments of the invention, are given by way of illustration only and not in a limiting way. Various changes and modifications within the spirit and scope of the invention will become apparent to those skilled in the art from the detailed description. Any combination of the features of the different embodiments disclosed herein that appear reasonable to a person of skill are comprised by the gist and scope of the present invention.

The initial situation of the present invention was based on the fact that polydimethylsiloxane (PDMS) was the mostly used material for a sorptive extraction layer. PDMS with its rather hydrophobic character is actually a suitable extractant for many rather apolar or lipophilic (liposoluble) target molecules from an aqueous medium. It is also convenient that the PDMS affinity respectively the PDMS/water partition coefficients (equilibrium partition constants $K_{PDMS/W}$) are known for many substances, because they are approximately the same as for the octanol/water partition coefficient $K_{O/W}$ (also called P), which is known from the field of traditional two-phase liquid-liquid extraction. Pursuant to James Sangster: "Octanol-Water Partition Coefficients of Simple Organic Compounds", J. Phys. Chem. Ref. Data, Vol. 18, No. 3, 1989, 1111-1227, octanol was chosen as the most useful and representative lipophilic solvent for biological purposes. Due to the high numerical values, K is often expressed as the common logarithmic value logK (or P as logP). Sometimes the additional notation "apparent" is used ($K_{app}$ or $P_{app}$, respectively the log thereof) if the target molecule is an ionizable compound, because only the neutral (uncharged) form of the molecule can partition into the neutral hydrophobic phase. The apparent partition coefficient (also known as distribution coefficient D) is in such cases smaller than the true partition coefficient for the neutral molecule only, and corresponds to the fraction of the molecule that is unionized (depending on pH). In addition, admixing of water-soluble organic solvents to the aqueous phase reduces the partition constant too.

PDMS is well suited for the extraction of substances with a $logK_{O/W}$ of more than 3.0, preferably of more than 4.0, so that an extraction efficiency of 80-90% or more can be expected when using a microplate with coated wells. For substances with a $logK_{O/W}$ of 3.0 or lower (which are less lipophilic), the extraction efficiency and the overall recovery however are not satisfactory with PDMS. The other materials known up to now for a sorptive extraction layer are not optimal either.

According to the invention, as a good alternative sorptive extraction layer material for immobilized liquid extraction of target molecules from biological samples, ethylene-acrylate-copolymer was found. A copolymer with this composition was not known before for this purpose. An ethylene-acrylate-copolymer is a statistical copolymer which comprises both apolar ethylene monomer units and polar acrylate monomer units. Ethylene-acrylate-copolymer is therefore in its average property a medium polar polymer, which is higher in its polarity than PDMS, but lower than a conventional polyacrylate. In contrast to an ethylene-acrylate-copolymer, a conventional polyacrylate is a polymer of acrylate monomers only and is a very polar phase. Due to this intermediate position (neither extremely lipophilic nor extremely polar) of ethylene-acrylate-copolymer, an efficient back-extraction (elution) is al-ways possible with a suitable solvent, because the partition equilibrium is not too strong on the polymer side. On the other hand a good affinity is achieved to such target molecules which in addition to a rather lipophilic body exhibit polar groups such as carboxylic acid groups or carbonyl groups.

When carrying out tests regarding the extraction velocity or the sorption equilibrium, the concentration of the target molecule in the liquid sample is measured as a function of the extraction time t. Usually the concentration is measured by UV spectroscopy (UV/VIS-absorbance), which gives the remaining (decreasing) concentration c(t) of the analyte in the supernatant solution during the extraction. The initial concentration before the beginning of the extraction (before the sample is brought in contact with the sorptive extraction layer) is $c_0$, which corresponds to the concentration at t=0 of the curve. The following characteristic parameters can then be calculated (please see cited review-article by E. Baltussen et al.):

Absorption A into polymer phase=$m_E(t)/m_{tot}=[c_0-c(t)]/c_0$

This gives the absorption (extraction) kinetics curve A as f(t). For long extraction times, the absorption A approaches the equilibrium and corresponds to the extraction efficiency η. A is usually expressed as a percentage (%).

The equilibrium concentration $c_{eq}$ leads to $(m_E/m_S)_{eq}=(C_0-C_{eq})/C_{eq}$ A multiplication of $(m_E/m_S)_{eq}$ with β gives the equilibrium constant K according to the basic equation. The common logarithm logK can then be indicated. If the analyte is ionizable, or if the solvent of the sample was not pure water but included also organic solvents, salts, or pH modifying agents, the additional notation "apparent" is used, e.g. log $K_{app}$ in order to indicate special circumstances.

The following examples illustrate the good extraction properties of ethylene-acrylate-copolymer as sorptive extraction layer material compared to conventional polydimethylsiloxane (PDMS) for certain types of analytes. Ethylene-acrylate-copolymer can of course also be used with good results for analytes which have a high $K_{O/W}$ or high logP value, such as Vitamin D (D2 and D3, D3 also named Cholecalciferol). Especially advantageous is however the use of ethylene-acrylate-copolymer as sorptive extraction layer material for target molecules which have a $logK_{O/W}$ of not more than about 3.5 and which exhibit a polar group, e.g. steroids.

In special cases inorganic molecules such as borazine or substituted borazines might also be target molecules of interest for the present invention.

As sorptive extraction layer materials according to the invention, amorphous ethylene-methylacrylate-copolymers (elastomers) were used in the tests. The three commercially available types Vamac® G, Vamac® DP and Vamac® GLS (which have been applied in automotive and industrial tubing so far; Vamac® being a trademark of DuPont) were used for the sorptive extraction layer in coated microplate wells for carrying out sorption equilibrium measurements with Naproxen and Ibuprofen, which are summarized in table 1. Vamac® G and Vamac® GLS are terpolymers of ethylene, methylacrylate and a small amount (4 mol-%) of a curesite monomer (acrylic acid), the latter allowing a diamine-based vulcanization (cross-linking) if desired or required for increased long-term stability. The present experiments were done with cross-linked Vamac® G. Vamac® DP is an ethylene-methylacrylate-dipolymer. The content of methylacrylate (MA) in these copolymers is indicated in table 1.

The analytes selected for the tests of table 1 were Naproxen (with a reported logP of approximately 3.0, exhibiting a carboxylic acid group) and Ibuprofen (with a reported logP of approximately 3.8, exhibiting a carboxylic acid group), while Testosterone (exhibiting a carbonyl group) was used for the further tests. Naproxen and Ibuprofen are non-steroidal anti-inflammatory drugs, whereas Testosterone is a steroid hormone from the androgen group.

To ensure sensitive UV measurement conditions for the target molecules Naproxen and Ibuprofen in the liquid, methanol had to be added to the aqueous phase of the samples relating to table 1. The extraction was performed at neutral pH.

TABLE 1

| Extraction layer | Analyte | |
| --- | --- | --- |
|  | Naproxen (40 vol-% MeOH) | Ibuprofen (50 vol-% MeOH) |
|  | $\log K_{app}$ | |
| Vamac ® G (55 mol-% MA) | 1.52 | 1.41 |
| Vamac ® DP (58 mol-% MA) | 1.48 | 1.48 |
| Vamac ® GLS (69 mol-% MA) | 1.29 | 0.98 |
| PDMS | 0.20 | 0.27 |

The values for $\log K_{app}$ of table 1 show clearly, that sorptive extraction layers according to the invention give a significantly higher partition ratio compared to PDMS for the probed analytes. This means that the affinity of a sorptive extraction layer to these analytes is higher with a Vamac® copolymer compared to PDMS, and higher extraction efficiencies are achievable using such a copolymer according to the invention. Furthermore there seems to exist an optimum average polarity at around 55 mol-% methylacrylate content, because the copolymer Vamac® GLS with higher methylacrylate content gave slightly lower values, but still clearly greater than PDMS.

For manufacturing of coated microplates it is preferred (and was done so in the tests) that, before carrying out the coating, the commercial ethylene-acrylate-copolymers are first fractionated by performing an appropriate procedure with appropriate solvents, in order to get a clean polymer without impurities, additives and low-molecular content, which otherwise might disturb the extraction and the analysis. The pre-fractionated polymer is then used for applying the coating from a solution of the polymer by evaporating the solvent.

It is also possible to use ethylene-acrylate-copolymers with lower acrylate content and thus lower average polarity. Such copolymers, which are partially crystalline if the acrylate content is not higher than about 15 mol-%, are available under the trade name Elvaloy® AC (Elvaloy® being a trademark of DuPont). An example is Elvaloy® AC 1125, a copolymer of ethylene and methylacrylate with 25% by weight methylacrylate, that corresponds to 10 mol-% methylacrylate. The crystallites in such partially crystalline copolymers can give an additional size exclusion effect against large molecules such as proteins, which should not enter the sorptive extraction layer. Only the smaller target molecules should preferably partition into the polymer phase. Moreover it is possible to mix different types of ethylene-acrylate-copolymers (e.g. an amorphous one and a partially crystalline one), preferably by mixing respective polymer solutions for coating. By this way, average polarities also between the commercially available copolymer types can be obtained for the sorptive extraction layer.

Figure 1:
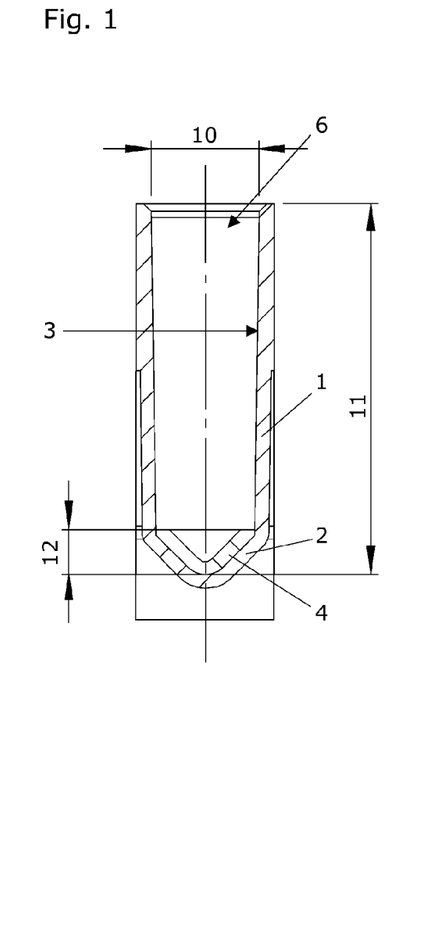
FIG. 1 a vertical cross-section of a single well of a 96 wells standard microplate, with bottom coating of the well.
Figure 2:
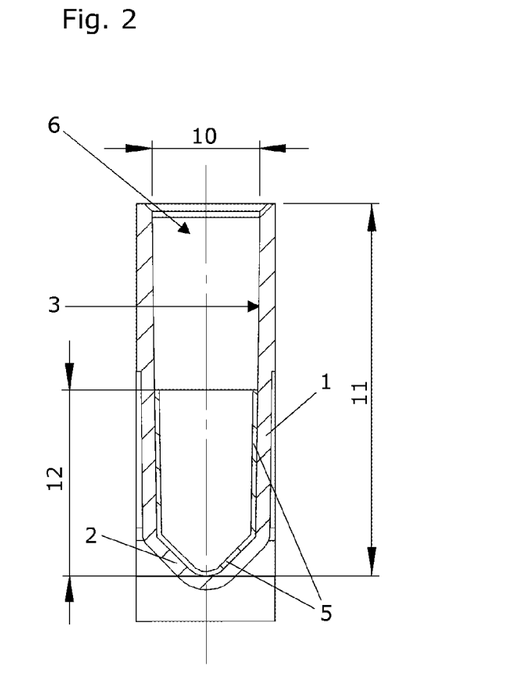
FIG. 2 a vertical cross-section of a single well of a 96 wells standard microplate, with bottom coating and wall coating until half height of the well.
Figure 3:
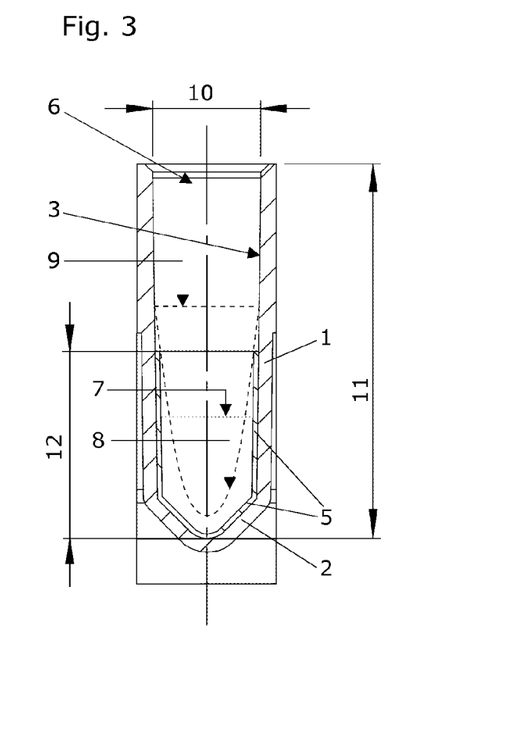
FIG. 3 the cross-section of FIG. 2 with added sample, the liquid level is indicated in the resting state and in the vortexed state.

Examples of a coated microplate well are shown in FIG. 1, FIG. 2 and FIG. 3. In each case, there is shown the vertical cross-section through a single well of a 96 wells standard microplate with deep wells and with a conical bottom. Of course the invention is not limited to this type of microplate and to this well shape; it is only an example for illustration. Each well has a wall (1), a bottom (2), and an inner surface (3). In the selected example, the inner diameter (10) of the well was 7 mm, and the inner height (11) of the well (from the lowest point of the bottom to the upper edge) was 24.2 mm. In FIG. 1 there is shown a bottom coating (4) with a sorptive extraction layer, i.e. only the inner surface in the area of the bottom was coated, the height (12) of the coating being indicated. In the selected example of this embodiment, the height (12) was 3 mm. In FIG. 2, which shows a particularly preferred embodiment of a well coating, the extraction polymer was spread over a larger area of the inner surface (3) of the well, so that a bottom plus wall coating (5) with a sorptive extraction layer is provided, thus the height (12) of the coating reaching considerably higher, and the bigger portion of the coating being in the area of the wall (1). In the selected example of this embodiment, the height (12) was 12.1 mm, i.e. corresponding to the half inner height (11) of the well.

For both embodiments of the coating, the same amount respectively the same volume of 5 μL (5 mm$^3$) polymer per well was used in the actual examples. The coated area in the case of bottom coating was about 50 mm$^2$, consequently the thickness of the bottom coating was about 0.1 mm. In the case of bottom plus wall coating according to FIG. 2, the totally coated area was about 250 mm$^2$, consequently the average thickness of the coating in this case was about 0.02 mm. The embodiment according to FIG. 2 is characterized by a large area of a very thin sorptive extraction layer, the large area being favourable for a fast mass transfer during extraction and elution.

FIG. 3 shows the well of FIG. 2, after a liquid sample was added through the opening (6) of the well. In the resting state, the liquid sample has a horizontal level (7), which is lower than the height (12) of the coating. In order to achieve a high extraction velocity for the analyte in the sample, it is advantageous to apply agitating. The agitating is preferably orbital shaking with an appropriate microplate shaker. Mostly preferred is an orbital shaking which effects a vortexing of the liquid samples in the wells of the microplate. Such a vortex is schematically shown in FIG. 3 by the dashed line (8), which represents the vortex curve of the liquid level. It is a rotating vortex, thus providing a relative velocity between the wall coating and the rotating liquid. The result is a diminished boundary layer between the sample in the well and the sorptive extraction layer, thus reducing the diffusion path for the analyte from the liquid bulk to the sorptive extraction layer and giving a fast extraction. Vortexing is of course also favourable for the washing step and the back-extraction step (elution). In the vortexed state, the wetted vortex level (9) at the inner surface (3) of the well is higher than the height (12) of the coating, thus the whole coating is wetted and utilized fully. In the actually selected example, the volume of the added liquid sample was 200 µL. This sample volume is typical for this well size. With relation to the volume of the polymer phase, a β value of 200/5=40 results. This is a very good precondition for a quantitative extraction.

Microplates with coated wells according to FIG. 1 respectively to FIG. 2 were used for extraction experiments with Testosterone. Shaking (vortexing) according to FIG. 3 was applied in all experiments (also with the bottom coated wells).

Figure 4:
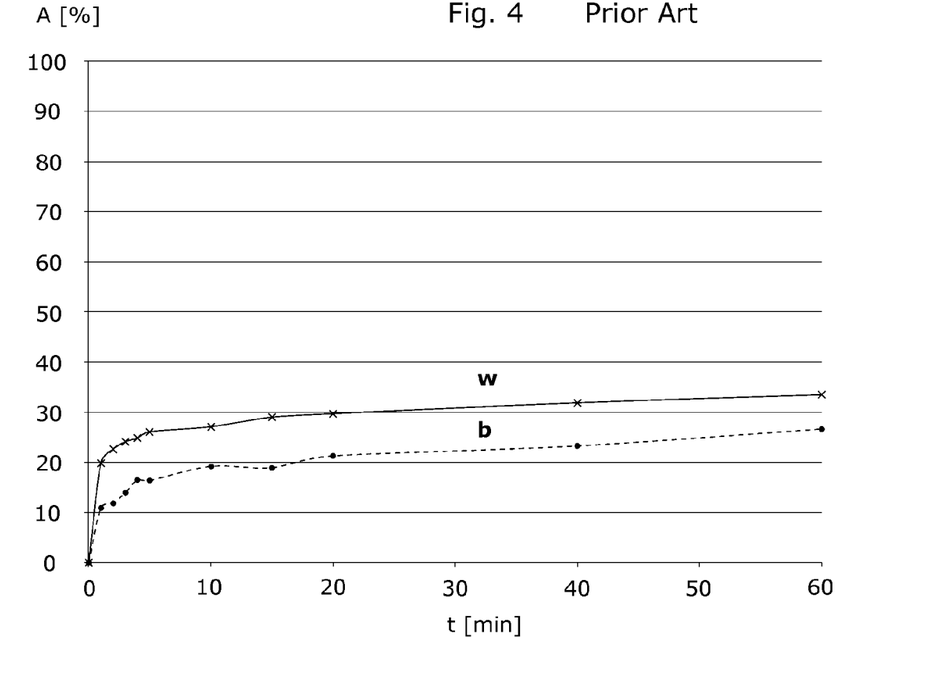
FIG. 4 extraction kinetics curves for testosterone, with PDMS (corresponding to prior art) as sorptive extraction layer, bottom coated (●), bottom plus wall coated (x), both with shaking.

For the measurement of the extraction kinetics, the 200 µL aqueous samples contained 16 vol-% acetonitrile (ACN) and 0.3 vol-% formic acid in water, and 16 ng/mL Testosterone. FIG. 4 shows the measurement of extraction kinetics curves for Testosterone as the target molecule, with a prior art sorptive extraction layer of PDMS. The diagram shows the course of the absorption A into the polymer phase as a function of extraction time t (in minutes). A is the absorbed mass of Testosterone in % related to the total mass of Testosterone in the system. Curve b was measured with a bottom coated well (according to FIG. 1), curve w with a bottom plus wall coated well (according to FIG. 2). The w curve increases faster, but both curves stagnate at a level of only about 30% absorption with the PDMS phase.

Figure 5:
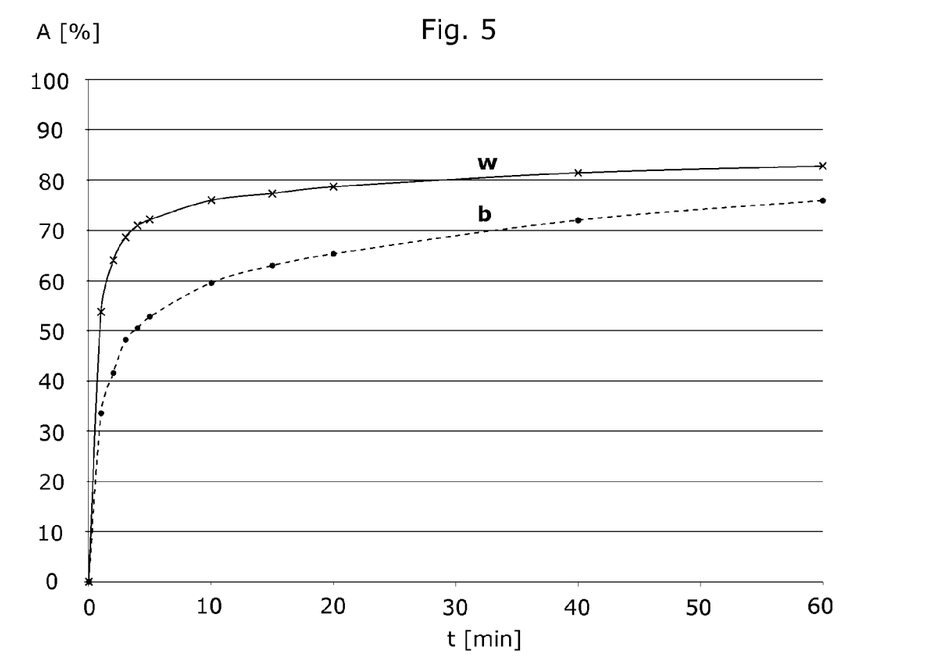
FIG. 5 extraction kinetics curves for testosterone, with an amorphous ethylene-methyl-acrylate-terpolymer (according to the invention) as sorptive extraction layer, bottom coated (●), bottom plus wall coated (x), both with shaking.

FIG. 5 shows the analogous extraction kinetics curves for Testosterone with a sorptive extraction layer according to the invention, namely Vamac® G. It can be seen clearly, that the absorption is very fast and reaches an equilibrium value of about 80%. Especially the steep w curve shows an equilibration to a large extent after 10-20 minutes. Consequently 10 minutes extraction time is sufficient in practice. This is a substantial progress compared to prior art. The comparison of FIG. 5 with FIG. 4 shows the clear advantage of an ethylene-acrylate-copolymer sorptive extraction layer over a conventional PDMS layer using the example of Testosterone.

Figure 6:
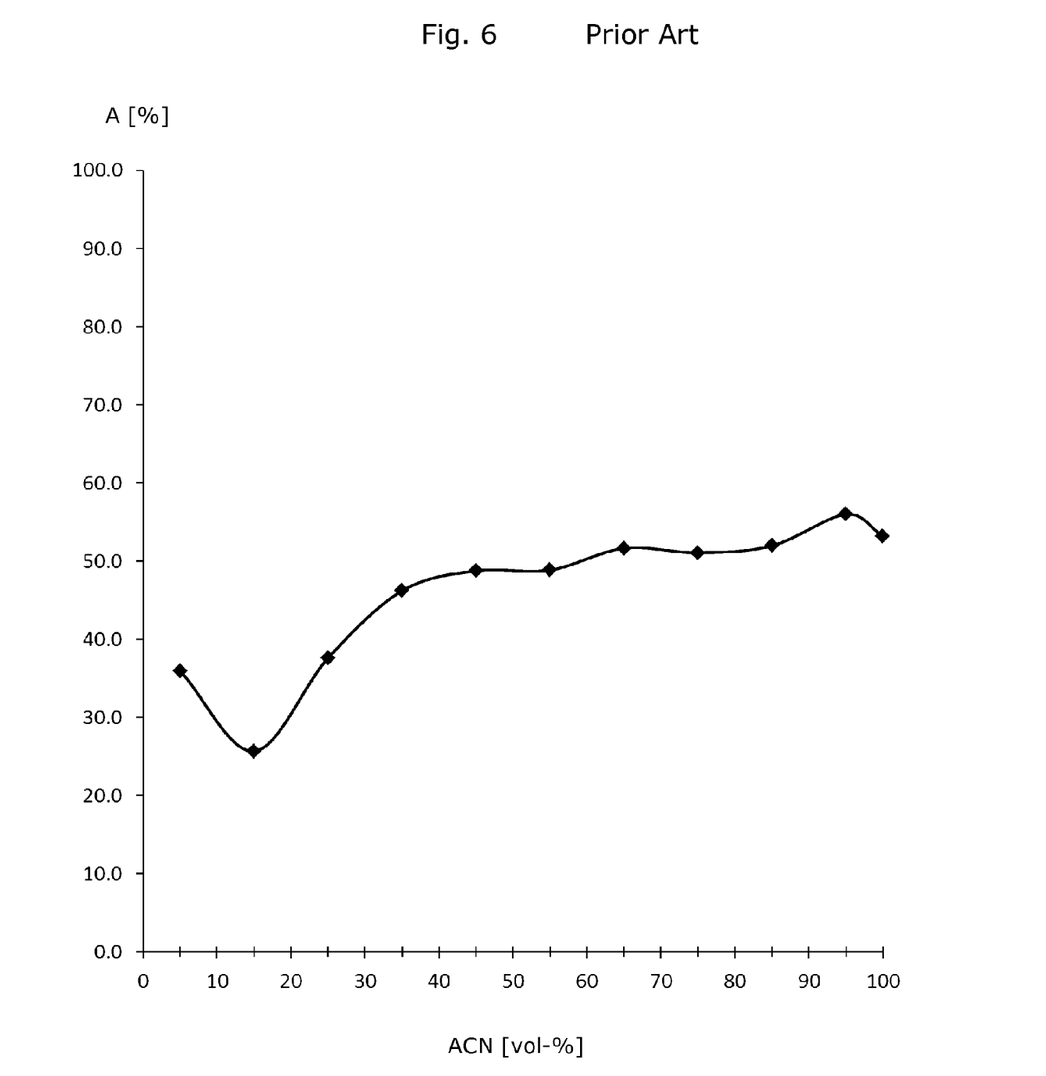
FIG. 6 DEEM (equilibrium) curve for testosterone/PDMS (corresponding to prior art) as a function of acetonitrile/water ratio in the liquid sample phase, measured in a coated well with β=50, the abbreviation DEEM means Direct Extraction Efficiency Measurement.

With FIG. 6 there is illustrated for Testosterone as analyte, that PDMS is not suitable over the whole range of ACN/water mixtures. This so-called DEEM curve shows the partition equilibrium for varying compositions of the extraction solvent mixture. In these liquid samples the formic acid concentration was 0.2 vol-%. The pH value was 2.5. A microplate with 4 µL (4 mm³) PDMS per well was used; so 13 was 50 in this case. The absorption (A) at the equilibrium corresponds to the extraction efficiency η. But at low ACN concentrations (usual sample conditions for extraction) no satisfactory extraction efficiency can be achieved. On the other hand, at high ACN-concentrations (which are usual for a back-extraction elution solvent), Testosterone cannot be sufficiently back-extracted from the PDMS phase and sticks to about 50% in the PDMS layer.

Figure 7:
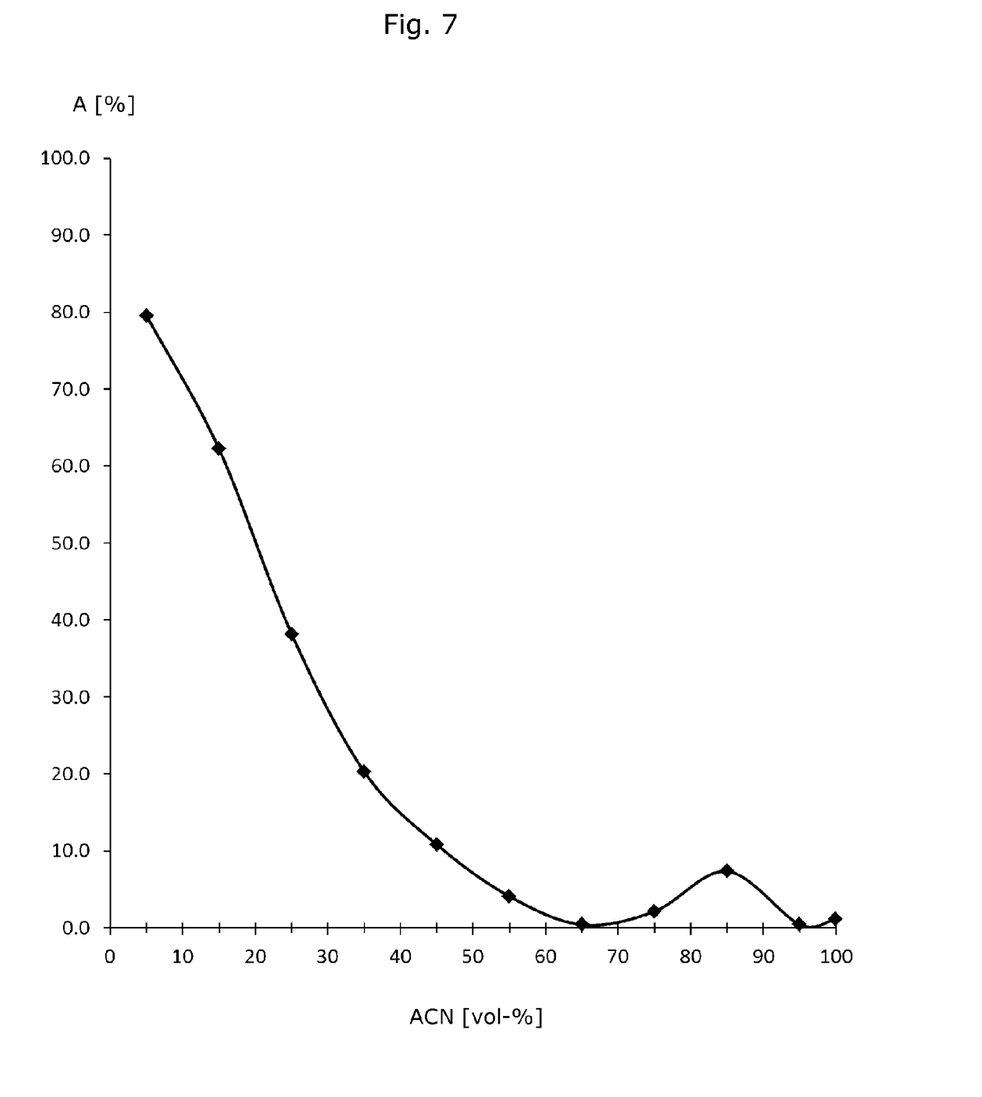
FIG. 7 DEEM (equilibrium) curve for testosterone/amorphous ethylene-methyl-acrylate-terpolymer (according to the invention) as a function of acetonitrile/water ratio in the liquid sample phase, measured in a coated well with β=40.

In contrast to the preceding figure, FIG. 7 shows a completely different and sophisticated DEEM curve, which has a sigmoid shape. A sorptive extraction layer according to the invention, namely Vamac® G, was used here for the equilibrium measurements with Testosterone as analyte. The test conditions were analogous to those of FIG. 6, but a microplate with 5 µL (5 mm³) Vamac® G per well was used; so β was 40. The DEEM curve of FIG. 7 really indicates a useful, optimal situation: At low ACN concentrations, a high extraction efficiency of 70-80% is achieved. This means that adding of a certain amount of ACN for releasing analytes and stabilizing the sample solution is possible without considerably lowering the extraction efficiency. On the other hand, at an ACN concentration of 65 vol-%, a practically complete back-extraction occurs and no Testosterone sticks to the polymer phase according to the invention.

Thus it was demonstrated that the present invention offers great advantages. Based on the prior art, it was not imaginable for someone skilled in the art to come to this invention.

The advantages of the present invention comprise:
A good affinity and extraction efficiency is achieved by a sorptive extraction layer, which is mainly composed of ethylene-acrylate-copolymer, to such target molecules which in addition to a rather lipophilic body exhibit polar groups such as carboxylic acid groups or carbonyl groups (cases where PDMS is not satisfactory).
Due to the medium polar property, an efficient back-extraction (elution) is always possible with a suitable solvent, because the partition equilibrium is not too strong on the side of the ethylene-acrylate-copolymer.
Cross-linking of a coating according to the invention can often be omitted, thereby the manufacturing of coated articles is simplified.
With accordingly coated microplates, the extraction velocity is enhanced and thus only short extraction times are necessary, if bottom and wall of the wells are coated (high surface area, thin layer) and vortexing is applied. Both factors together result in fast kinetics.
The extraction efficiency at the partition equilibrium is high due to large K and small β (even compared to SBSE, the conditions are beneficial).
Due to the well-balanced properties of a sorptive extraction layer, which is mainly composed of ethylene-acrylate-copolymer, extraction and back-extraction can be performed both with high efficiency by simply adjusting the ACN/water ratio to the suitable value for the respective step. In the extraction step, a certain amount of ACN promotes the release of analytes and avoids precipitation of possibly present proteins, without considerably deteriorating the extraction efficiency of an ethylene-acrylate-copolymer.
Coated microplates according to the invention enable a simplified and accelerated entire process which is suited for automation.

List of reference numerals and symbols in the figures:
1 wall of a microplate well
2 bottom of the microplate well
3 inner surface of the well
4 bottom coating with a sorptive extraction layer
5 bottom plus wall coating with a sorptive extraction layer
6 opening of the well
7 horizontal liquid level (in the resting state)
8 vortex curve of liquid level (rotating)
9 wetted vortex level at the inner surface of the well
10 inner diameter of the well
11 inner height of the well
12 height of the coating
A absorption into polymer phase (in % relating to the total mass of analyte)
t absorption (extraction) time (in minutes)
b absorption (extraction) kinetics curve with a bottom coated well
w absorption (extraction) kinetics curve with a bottom plus wall coated well
ACN acetonitrile (in vol-% in the aqueous phase)

What is claimed is:
1. A method of extracting target molecules from samples by immobilized liquid extraction, the method comprising:

providing a microplate array, the microplate array comprising a plurality of microplate wells;
wherein an inner surface of each microplate well comprises a bottom and a wall;
wherein at least part of the inner surface of each microplate well is coated with a sorptive extraction layer, said sorptive extraction layer comprising at least 90% ethylene-acrylate-copolymer by weight, wherein the ethylene-acrylate-copolymer comprises ethylene-acrylate-elastomer (AEM);
the method further comprising:
preparing at least one combined solution by mixing together a sample and an extraction solvent, wherein the extraction solvent comprises water and an organic solvent, and wherein the sample comprises target molecules; and
adding combined solution to at least one of said microplate wells to initiate an extraction step, with the sorptive extraction layer extracting target molecules from the combined solution during the extraction step.

2. The method of claim 1, wherein the organic solvent is selected from the group consisting of acetonitrile, methanol, ethanol, and isopropanol.

3. The method of claim 2, wherein the organic solvent is acetonitrile.

4. The method of claim 1, wherein the organic solvent concentration in the combined solution lies in a range between a minimum concentration of 10 vol.-% and a maximum concentration of 35 vol.-%.

5. The method of claim 1, wherein the extraction solvent mixture additionally comprises at least one substance selected from the group consisting of buffers, salts, pH modifying agents, and internal standards.

6. The method of claim 1 wherein the extraction step further comprises agitating the microplate array.

7. The method of claim 6,
wherein the sorptive extraction layer covers the bottom and at least a lower 40% of the wall of the inner surface of each of the plurality of said microplate wells;
wherein said agitation of the microplate array comprises vortexing; and
wherein said agitation is performed for not more than 20 minutes.

8. The method of claim 1,
wherein the extraction step is followed by a washing step and then by a back-extraction step, the back-extraction step releasing target molecules from the sorptive extraction layer;
wherein the back-extraction step comprises adding an elution solvent to at least one microplate well which previously received combined solution, the elution solvent comprising more than 50% organic solvent by volume and further comprising water; and
wherein target molecules are released from said sorptive extraction layer during the back-extraction step.

9. The method of claim 8, wherein agitation is applied during the washing step and the back-extraction step.

10. The method of claim 1, wherein the ethylene-acrylate-copolymer comprises a non-crystalline ethylene-acrylate-elastomer (AEM).

11. The method of claim 10, wherein the non-crystalline ethylene-acrylate-elastomer is a non-crystalline ethylene-methylacrylate-dipolymer.

12. The method of claim 10, wherein the non-crystalline ethylene-acrylate-elastomer is a non-crystalline ethylene-methylacrylate-terpolymer.

13. The method of claim 1, wherein the ethylene-acrylate-copolymer comprises a partially crystalline ethylene-acrylate-copolymer.

14. The method of claim 13, wherein the partially crystalline ethylene-acrylate-copolymer comprises a partially crystalline ethylene-methylacrylate-copolymer.

15. The method of claim 1, wherein at least a part of the bottom of at least a part of the wells is coated with the sorptive extraction layer.

16. The method of claim 15, wherein the bottom and at least a portion of the wall of a plurality of microplate wells are coated with the sorptive extraction layer.

17. The method of claim 1, wherein the sorptive layer has a mean thickness in the range of 10 μm to 100 μm.

18. A method of extracting target molecules from biological samples, the method comprising:
providing a microplate array, the microplate array comprising a plurality of microplate wells, each microplate well comprising an inner surface;
providing at least one biological sample;
wherein at least part of the inner surface of each microplate well is coated with a sorptive extraction layer, said sorptive extraction layer comprising at least 90% ethylene-acrylate-copolymer by weight, wherein the ethylene-acrylate-copolymer comprises ethylene-acrylate-elastomer (AEM);
the method further comprising:
preparing at least one combined solution by mixing together the biological sample and an extraction solvent, wherein the extraction solvent comprises water and an organic solvent, and wherein the biological sample comprises target molecules; and
adding combined solution to at least one of said microplate wells to initiate an extraction step, with at least some of the target molecules entering and being dissolved in the sorptive extraction layer during the extraction step.

19. The method of claim 18,
wherein the extraction step is followed by a washing step and then by a back-extraction step, the back-extraction step releasing target molecules from the sorptive extraction layer;
wherein the back-extraction step comprises adding an elution solvent to one or more microplate wells which previously received combined solution, the elution solvent comprising more than 50% organic solvent by volume and further comprising water; and
wherein target molecules are released from said sorptive extraction layer during the back-extraction step.

20. The method of claim 18, wherein at least one biological sample comprises a body fluid.

* * * * *